US006280603B1

(12) United States Patent
Jovancicevic (10) Patent No.: US 6,280,603 B1
(45) Date of Patent: Aug. 28, 2001

(54) ELECTROCHEMICAL NOISE TECHNIQUE FOR CORROSION

(75) Inventor: Vladimir Jovancicevic, Richmond, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 09/457,986

(22) Filed: Dec. 9, 1999

Related U.S. Application Data

(60) Provisional application No. 60/111,735, filed on Dec. 10, 1998.

(51) Int. Cl.[7] .................................................. G01N 17/04
(52) U.S. Cl. ........................................................ 205/775.5
(58) Field of Search ........................... 205/775.5; 204/404

(56) References Cited

U.S. PATENT DOCUMENTS 3,716,460  2/1973  Weisstuch et al. .................. 204/404
5,139,627  8/1992  Eden et al. ........................... 204/404

FOREIGN PATENT DOCUMENTS 2218521A    11/1989  (GB) .
WO98/50786  11/1998  (WO) .

*Primary Examiner*—Bruce F. Bell
(74) *Attorney, Agent, or Firm*—Cantor Colburn LLP (57) ABSTRACT

The present invention relates to a unique electrochemical noise corrosion rate determination technique and system. The system employs a single working electrode, a counter electrode, a reference electrode, and a measurement system for determining potential between the working and reference electrodes and current between the working and counter electrodes. The technique comprises measuring the potential between the working and reference electrodes at open circuit over a given period of time, switching to potentiostatic control, measuring the current between the working and counter electrodes, and using the measured potential and current to determine the general corrosion rate and localized corrosion rates.

14 Claims, 6 Drawing Sheets

ELECTROCHEMICAL NOISE TECHNIQUE FOR CORROSION

RELATED APPLICATIONS

Priority is hereby claimed to U.S. Provisional Application Ser. No. 60/111,735, filed on Dec. 10, 1998, which is incorporated herein by reference.

TECHNICAL FIELD

The present invention relates to an electrochemical noise technique for determining corrosion rate.

BACKGROUND OF THE INVENTION

Electrochemical noise (ECN) may be defined as the spontaneous fluctuations of current and potential generated by corrosion reactions. Various methods have been used to detect corrosion reactions, including a linear polarization resistance method in which a direct current (DC) signal is applied to a corroding cell consisting of two or three electrodes and the resulting DC polarization is monitored. Provided that the applied current is small so that the potential shift is less than 20 millivolts (mV), the response is linear in most cases and the measured resistance, commonly known as the polarization resistance, may be related inversely to the rate of the uniform corrosion attack. Other techniques include the application of electrochemical impedance in which a sine wave current or potential is applied, in a similar manner to the linear polarization technique, and the sine wave potential or current resulting from the applied current or potential is monitored. Alternatively, a pseudo random noise signal can be applied to a corroding cell, with the electrochemical impedance obtained by time or frequency domain transformations.

Although the above techniques are widely employed, they: (1) possess limitations in that they only provide information on uniform corrosion conditions because they provide an average signal for the surface of the electrode being monitored; and (2) depending upon the environment, metallic material, and corrosion type, the assumption that me corrosion rate is proportional to the measured charge transfer or polarization resistance is invalid because the corrosion is of a localized nature. These problems have been addressed by monitoring localized corrosion via the utilization of electrochemical potential noise analysis. Alternatively, by coupling current analysis with electrochemical potential noise analysis further information can be obtained. For example, two similar electrodes can be coupled together via a zero resistance ammeter with the output of the zero resistance ammeter passed to the input of the electrochemical noise analysis system. In this way, the fluctuation of the coupling current may be analyzed in essentially a similar manner as for the electrochemical potential noise analysis described previously.

U.S. Pat. No. 5,139,627 to Eden et al. discloses a system which employs two working electrodes fabricated with the same material and exposed to the same corrosion conditions as the metallic surface to be tested. This system further employs means for measuring the coupling current between the working electrodes, means for measuring electrochemical potential noise originating from the electrodes, and means for comparing the coupling current with the electrochemical current noise to provide an output indicative of the degree to which corrosion is localized. Eden et al. utilize open circuit potential conditions, employing two working electrodes in an electrolyte environment wherein both electrodes are short circuited with a low resistance amp meter. The current between these two working electrodes is the result of corrosion occurring on them, with the measurement of the net current relating to the corrosion on both of them. Disadvantages of this system, however, range from the fact that the working electrodes need to be identical to obtain accurate readings and obtaining such identical electrodes is difficult, if not impossible, and also that it is unknown which electrode is responding to reveal the corrosion, to the fact that this system requires the use of two working electrodes which limits where this system can be employed. Furthermore, distinguishing between various types of localized corrosion is, at minimal, difficult due to the fact that both electrodes contribute to the system response.

What is needed in the art is a simplified corrosion rate detection system and method.

SUMMARY OF THE INVENTION

The present invention relates to an electrochemical noise method for determining the corrosion rate of a conductive article, comprising: placing a working electrode, reference electrode, and counter electrode in a corrosive environment of interest, wherein said working electrode has substantially the same composition as the article; measuring potential at open circuit between the working electrode and the reference electrode over a first period of time; placing the working electrode under a potentiostatic control; and measuring current between the working electrode and the counter electrode for second period of time.

The present invention further relates to a working electrode which is composed of the material of interest; a counter electrode which is inert in an environment of interest; a reference electrode which is inert in the environment of interest; and a measurement system connected to said working electrode, counter electrode, and said reference electrode, wherein said measurement system is capable of monitoring potential between said working electrode and said reference electrode and monitoring current between said counting electrode and said working electrode.

BRIEF DESCRIPTION OF THE DRAWINGS

Referring now to the drawing, which is meant to be exemplary, not limiting.

BEST MODE FOR CARRYING OUT THE INVENTION

The present invention relates to determining corrosion rate on a metallic surface using a unique electrochemical noise technique. The present invention employs one working electrode where potential created by the corrosion of that electrode in the corrosive fluid is measured relative to a reference electrode over a distinct period of time; the working electrode is then set at the measured potential, and, without applying a potential ($\Delta V=0$), the working electrode is placed in potentiostatic control; and subsequently, the current between the working electrode and the counting electrode is measured for a second period of time. The cycle is repeated after the current measurement. Finally, the measured current and potential are used to determine the general and localized corrosion rate.

In order to determine the corrosion rate, the working electrode is fabricated from the same material as the item of concern (i.e. the component, article . . . ). Generally, the material is a metal or metal alloy. Although the counter electrode can be formed of any material, including the same material as the working electrode, the counter electrode preferably comprises material which is inert in the particular environment of interest For example, the counter electrode may be platinum, nickel-based (e.g., Hastalloy C276), iron based (e.g., stainless steel) or a chromium-based alloy, or mixtures and alloys thereof, or any other electrically conductive, non-corrosive material. Similar to the counter electrode, the reference electrode can comprise any material, but preferably comprises an inert, electrically conductive material which may be the same or a different material as employed by the counter electrode.

In operation, the working, counter, and reference electrodes are disposed in the same environment as the component of interest, in a spaced relation to one another. A potential between the working and reference electrodes is measured first at open circuit potential for a certain period of time. The period of time, which can be any length of time, is typically less than 1 minute, and preferably less than about 10 seconds (sec.), with less than about 1 sec. especially preferred for convenience and reduced testing time. At the end of the period of time, a potential equivalent to the measured potential at that time, is then applied to the working electrode by switching from open circuit to potentiostatic control. Once potentiostatic conditions have been established, the current between the working electrode and the counter electrode can be measured for a second period (although this second period of time can be any period, the same amount of time is preferred). A new cycle can then be performed after the potentiostatic current measurement.

The measured potential and current noise can then be utilized to determine the general and localized corrosion rate using conventional calculation techniques which typically use the average current (root mean square ($RMS_i$)) and average potential ($RMS_V$) and standard deviation of current ($\sigma_i$). For example, general corrosion ($I^G_{corr}$) is known to be related to resistance noise ($R_N$) as follows:

$$I^G_{corr} \propto \frac{1}{R_N} \quad \text{where} \tag{1}$$

$$R_N = \frac{\sigma_V}{\sigma_i} \tag{2}$$

while localized corrosion ($I^L_{corr}$) is a function of the electrochemical current noise ($\sigma_i$) as follows:

$$I^L_{corr} \, \sigma_i$$

Figure 1:
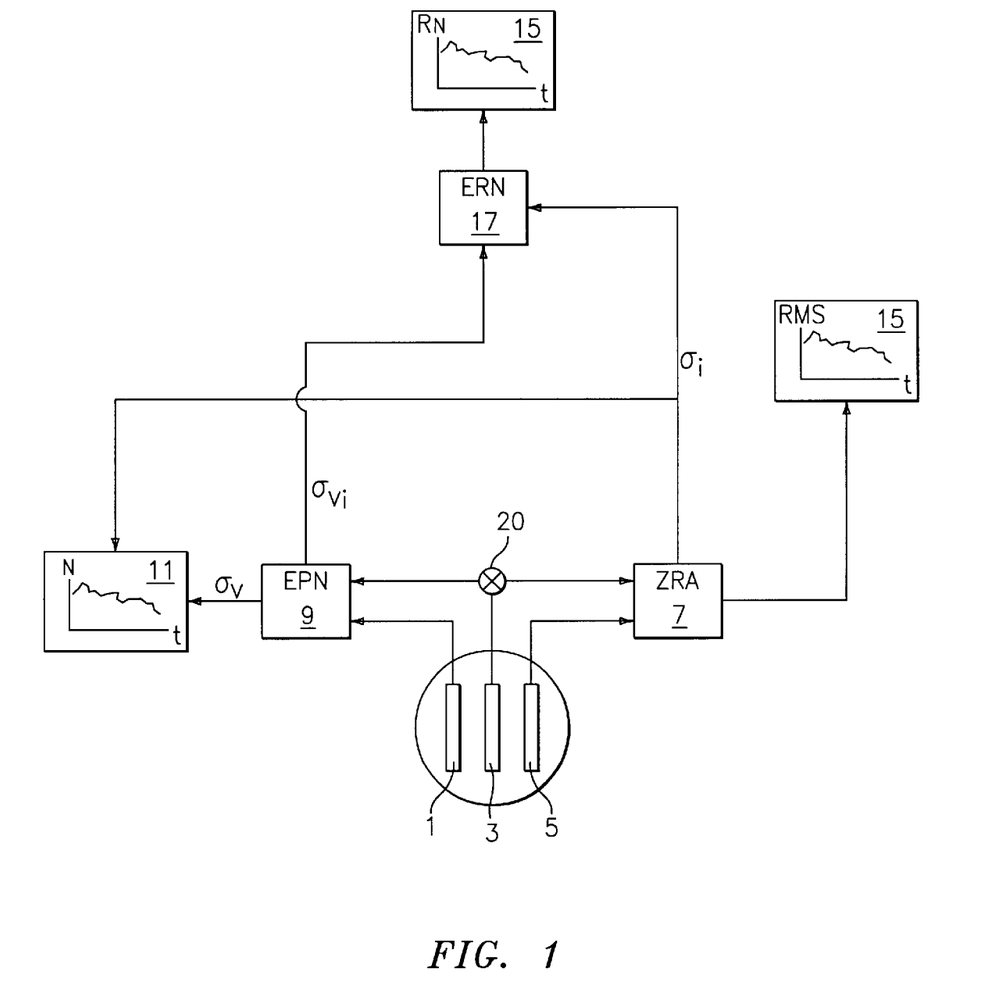
FIG. 1 is a schematic of one embodiment of the electrochemical noise system of the present invention.

Referring to FIG. 1, which illustrates one potential embodiment of the present invention, a working electrode 3 is disposed between and in spaced relation to both reference electrode 1 and counter electrode 5. The counter electrode 5 and working electrode 3 are connected to a potentiostat 7 which feeds into comparator 17 ($R_N$) and a localized corrosion measurement device 15 capable of measuring localized corrosion as a function of time. Meanwhile, reference electrode 1 and working electrode 3 are connected to electrochemical potential noise monitoring apparatus 9 (i.e., voltmeter) which feeds into comparator 17 and power density analyzer 11. From that input, in combination with input from the electrochemical current noise measuring apparatus 7, localized corrosion rate can be determined. Electrochemical potential noise monitoring apparatus 9 additionally feeds input to comparator 17 to determine general corrosion rate as a function of time.

EXAMPLE 1

The following example is the measurement of corrosion rate for a mild steel (e.g., ASTM steel C1018) in a mixture of brine, hydrocarbon, and carbon dioxide environment using the embodiment shown in FIG. 1.

The counter and reference electrodes are Hastalloy C276 (commercially available from Metal Samples, Inc., GA), while the working electrode is mild steel C1018.

The electrodes 1, 3, 5 are disposed in the brine, hydrocarbon, and carbon dioxide. After the potential is measured for 10 sec., between the working and reference electrodes at open circuit, the potential is then fixed ($\Delta V=0$) and the current is measured between the working and counter electrodes for 10 seconds, while the potential between the working electrode 3 and the reference electrode 1 is measured by the high sensitivity, high resistance voltmeter 9.

Consequently, the present invention employs the potential and current noise to determine general corrosion rate (from $R_N$) and the current noise to quantitatively assess the degree and nature of localized corrosion from the pattern recognition analysis.

EXAMPLE 2

Figure 2:
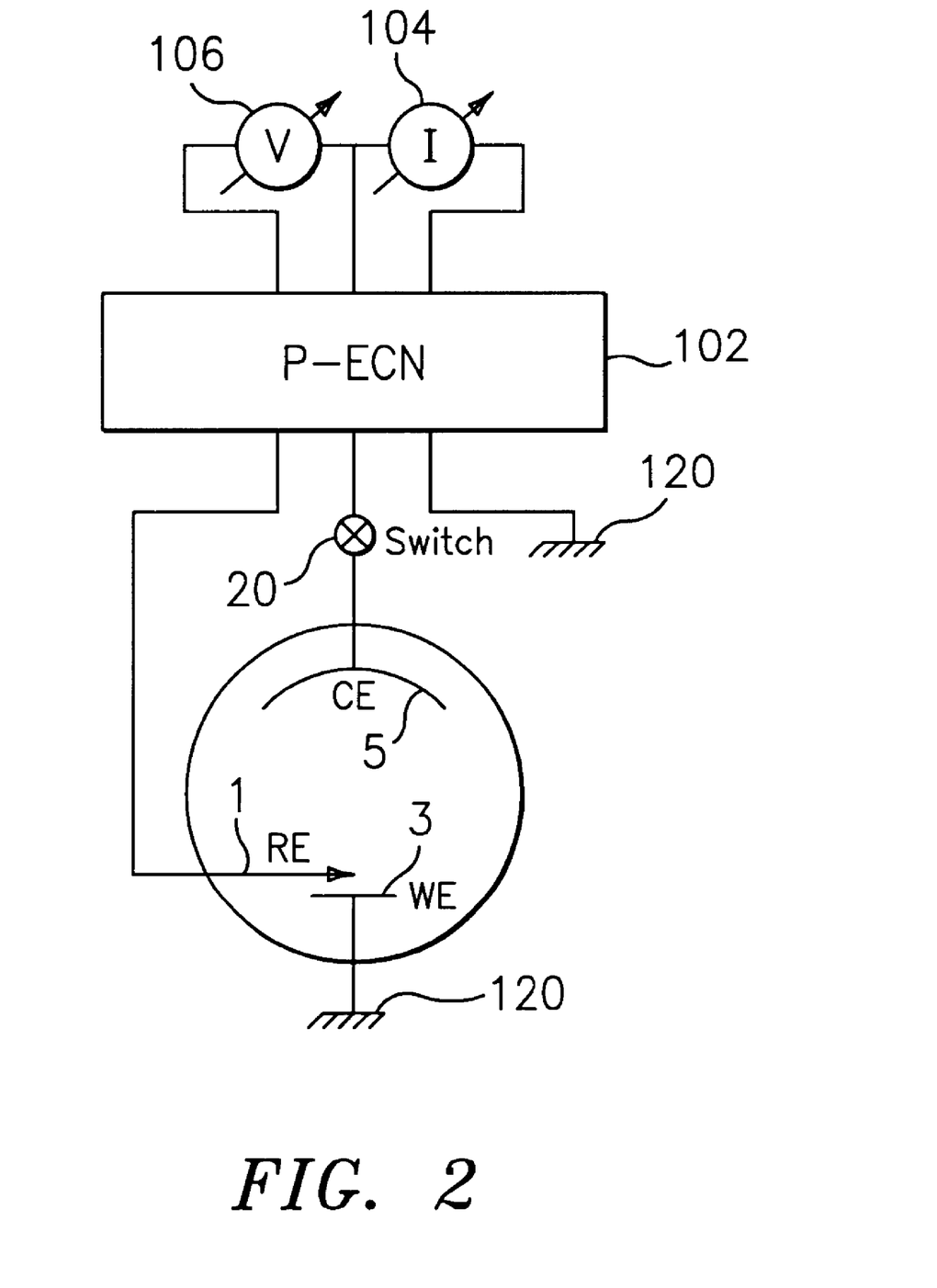
FIG. 2 is a schematic of another embodiment of the electrochemical noise system of the present invention.

The current and potential noise data were sampled between a 1 and 60 second period with current being measured when potential was held and the potential measured with the current open-circuit. The standard mode of operation used the system illustrated in FIG. 2, and consisted of the following sequence:

1. Measure the potential between working and reference electrode (1 to 60 sec.)—period A;
2. Record the potential at the end of period A;
3. Hold the potential (0.1 to 60 sec.)—period B;
4. Measure and record the current at the end of period B;
5. Release the potential hold (0 to 60 sec.)—period C; and
6. Return to '1'.

Figure 3:
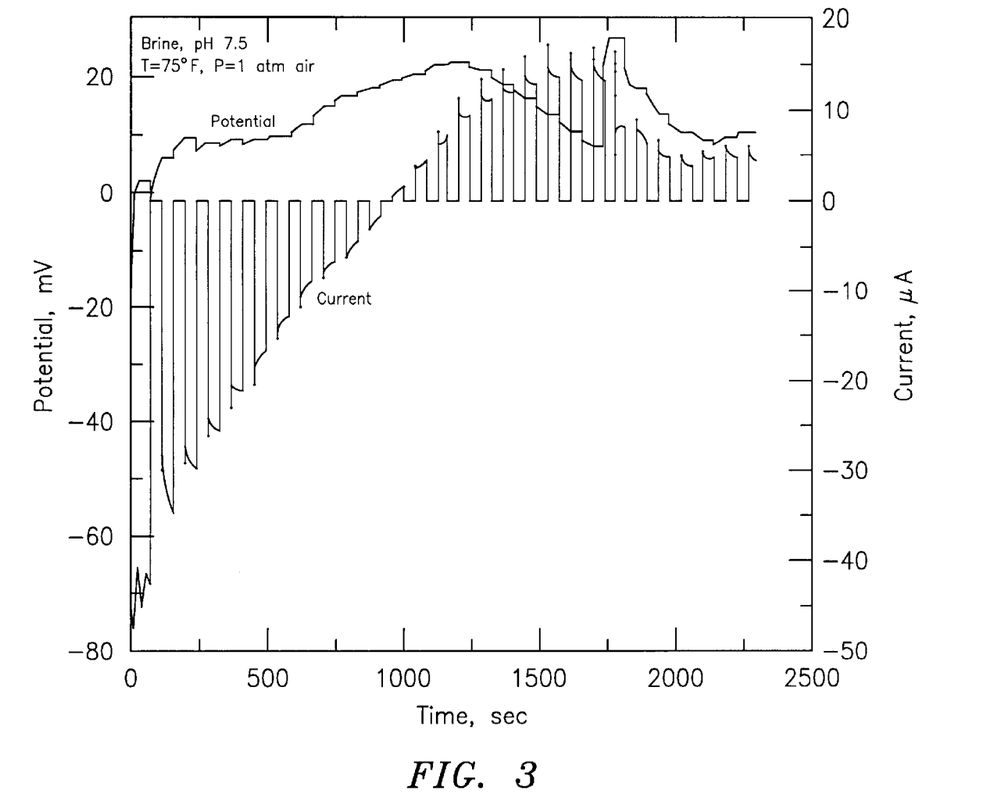
FIG. 3 is a graphical representation of potential/current versus time raw data plot for potentiostatic ECN in brine/air.
Figure 4:
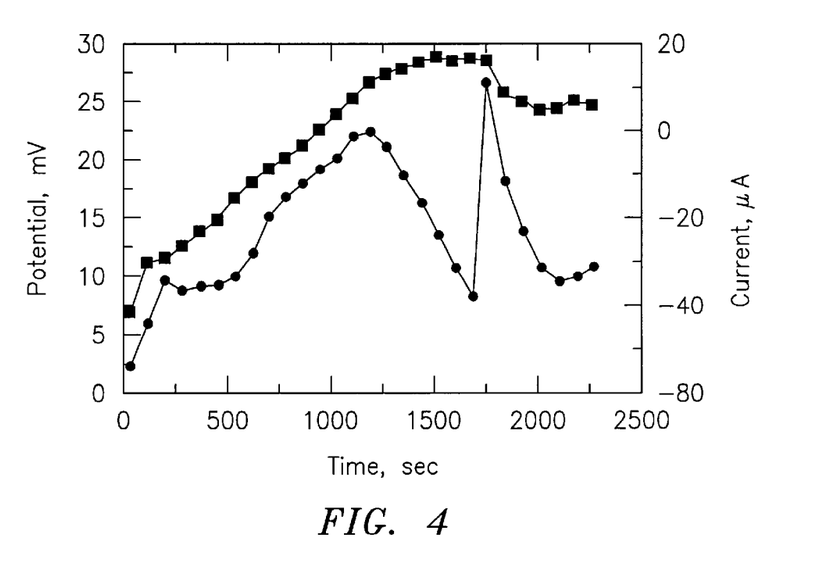
FIG. 4 is a graphical representation of potential/current noise data versus time raw data plot for potentiostatic ECN in brine/air.

FIG. 3 shows the potential/current versus time curves in a brine/air solution obtained with the potentiostatic ECN (P-ECN) technique. The time periods chosen for this test were A equals 40 seconds, B equals 40 seconds, and C equals 0. During the potential hold off period (A), the potential was measured and the current was zero. During the potential hold on period (B), the potential was constant (potential noise value) and the current was measured. The initial increase in current was due to the double layer capacitive current followed by a continuous increase/decrease in anodic/cathodic current. The first value after the initial current increase was recorded (current noise) and plotted together with the potential noise as shown in FIG. 4. It is important to note an increase in potential noise at about 1,700 seconds that coincided with a decrease in current noise, suggesting a good correlation between the two. In this test run, due to the low sampling rate, high frequency noise was not observed.

Figure 5:
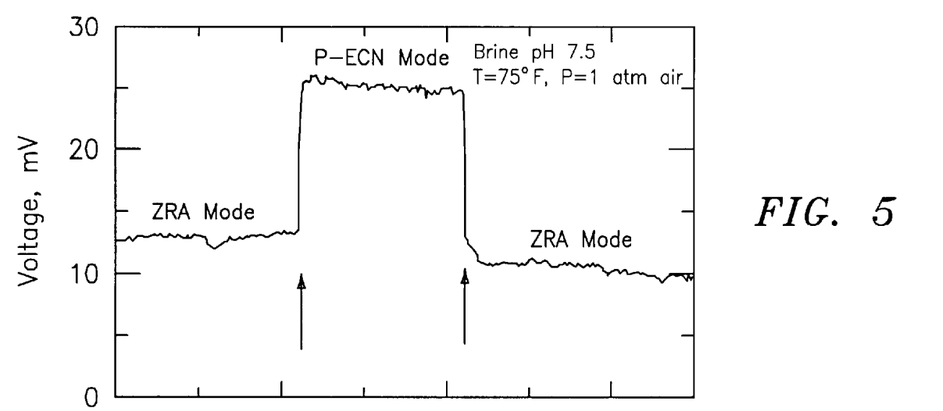
FIG. 5 is a graphical representation comparing potentiostatic ECN and zero resistant ammeter mode in brine/air solution for voltage versus time.
Figure 6:
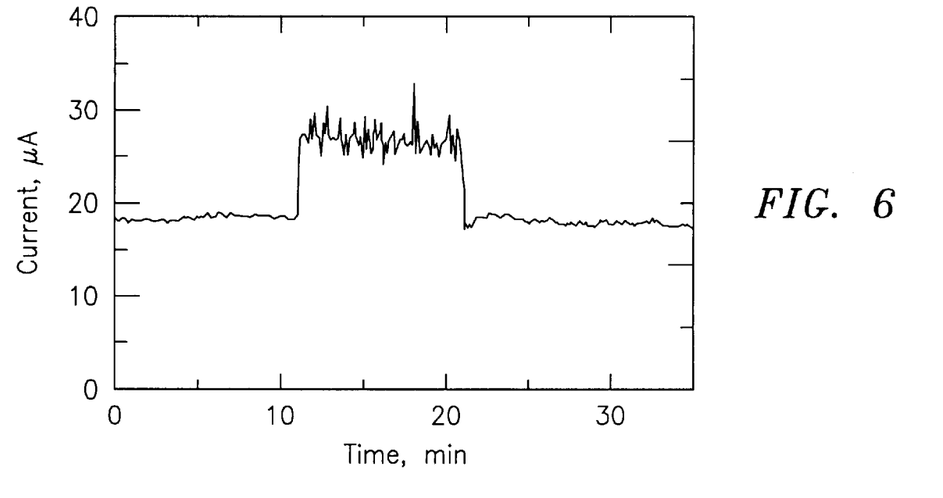
FIG. 6 is a graphical representation comparing potentiostatic ECN and zero resistant ammeter mode in brine/air solution for current versus time.

The comparison between the current and potential noise obtained with conventional ECN (zero-resistance mode (ZRM)) and potentiostatic ECN in brine/air solution was shown in FIGS. 5 and 6. In this system, the corrosion rate was quite high with one working electrode corroding at a higher rate than the other electrode ($\Delta V=13$ millivolts (mV) in ZRM). In the potentiostatic mode, both current and potential noises increased significantly (increase in rms and standard deviation) due to an increase in corrosion rate. This result showed that the second working electrode was polarizing the 'real' working electrode by $-12$ mV in the ZRA mode, thus lowering the corrosion rate by at least factor of two compared to the potentiostatic mode. This polarization of the working electrode over long period of time may have significant effect on the measured corrosion rate. Thus, in this case both general and localized corrosion rates were significantly higher when measured by the potentiostatic ECN. The corrosion rate measurements at the open-circuit potential, without induced polarization, was an important advantage of the potentiostatic ECN relative to the ZRA mode. If the second electrode in the couple had been selected for the potentiostatic ECN it would be expected that the potential and current would both have dropped. This confirms that in ECN monitoring there is an applied potential between the two 'non' identical electrodes.

The potentiostatic ECN technique was further evaluated for the effect of stirring and the addition of a corrosion inhibitor on current and potential noise in a carbon dioxide ($CO_2$)-containing brine solution. The parameters used in this study were, A equals 1 second, B equals 10 seconds, C equals 0 seconds.

Figure 7:
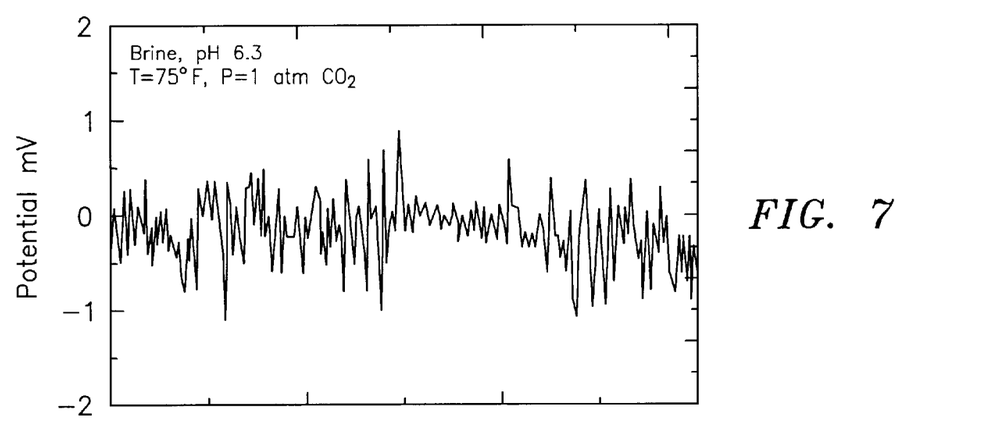
FIG. 7 is a graphical representation of potential versus time showing the effect of flow on current/potential noise in brine/carbon dioxide solution.
Figure 8:
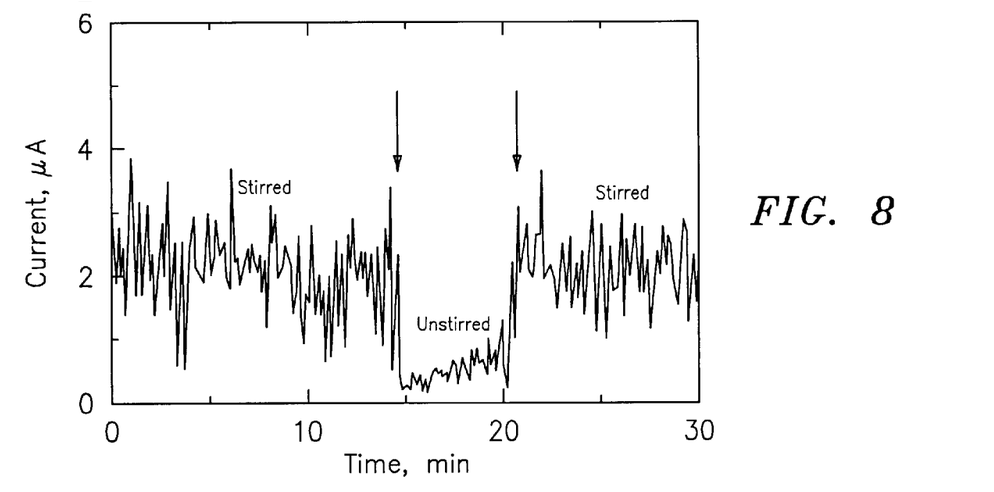
FIG. 8 is a graphical representation of current versus time showing the effect of flow on current/potential noise in brine/carbon dioxide solution.

FIGS. 7 and 8 show the current and potential noise in the brine/$CO_2$ solution with and without stirring obtained using the potentiostatic ECN technique. It can be seen that stirring (at about 100 revolutions per minute (rpm) or less) has a significant effect on current and potential noise resulting in ten-fold reduction in fluctuations (i.e. standard deviations). The root mean square (rms) of current noise was also decreased by a similar amount. Thus, the changes in current and potential fluctuations with time were related to changes in flow rate/flow regime in this particular system.

Figure 9:
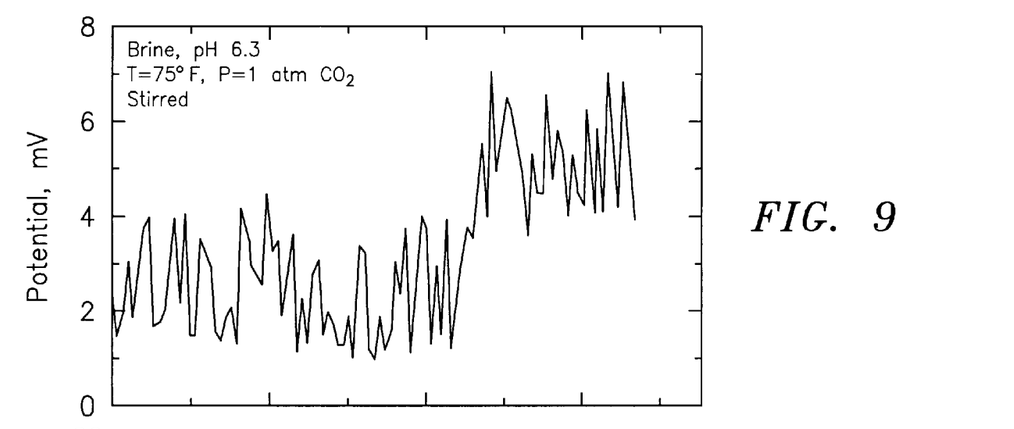
FIG. 9 is a graphical representation of potential versus time showing the effect of quaternary amine inhibitor on current/potential noise in brine/carbon dioxide solution.
Figure 10:
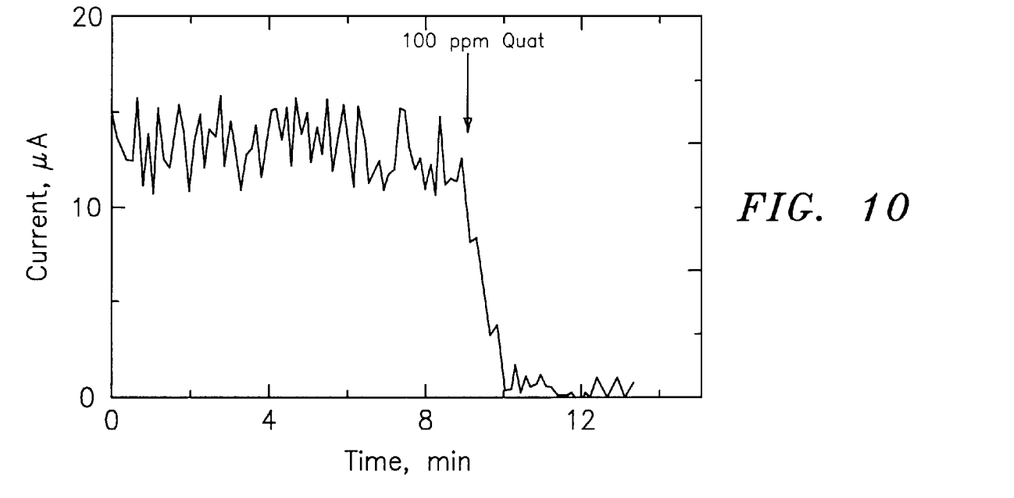
FIG. 10 is a graphical representation of current versus time showing the effect of quaternary amine inhibitor on current/potential noise in brine/carbon dioxide solution.

The effect of an inhibitor (e.g. quaternary amine) on the current and potential noise in stirred brine/$CO_2$ solution was shown in FIGS. 9 and 10. The addition of 100 parts per million (ppm) of quaternary amine resulted in a sudden decrease in current noise (rms) and significant reduction in current fluctuations ($\sigma_1$) indicating a reduction in general corrosion by about 95% (Table 1). At the same time, some increase in localized corrosion was observed ($\sigma_i/rms_i$ about 0.6). The results showed that in the P-ECN mode the corrosion rate reduction can be obtained either from the change in rms of current noise or from the noise resistance ($\sigma_V/\sigma_I$). In the ZRA mode only trends in corrosion rates can be obtained from the rms but not the absolute values. This is another important advantage of the P-ECN compared to the ZRA measurements.

TABLE 1

|  | $rms_V$ (mV) | $rms_I$ ($\mu A$) | $\sigma_V$ (mV) | $\sigma_I$ ($\mu A$) |
|---|---|---|---|---|
| Blank | 2.5 | 13.0 | 0.8 | 1.0 |
| quaternary amine | 5.0 | 0.5 | 0.9 | 0.5 |

The system of the present invention can be further simplified by automating the system using an appropriate computer system and software. The software should be able to control all necessary switching and measurements as described herein. By automating the current system, error introduced due to human interaction and delay can be eliminated.

The present invention is a simplified corrosion measurement system and method. Unlike the prior art which requires the use of two identical working electrodes formed of the same material as the article, the present invention utilizes one working electrode (different counter and reference electrodes), thereby eliminating error created by differences between the electrodes since all the measured data are from the same electrode. Additional advantages include that there is an improved correlation between the current and potential noise (i.e. same source); corrosion rate is measured at open circuit potential (OCP) without disturbing the system; and there is little or no loss of long-term current/potential drift signal (DC components). Furthermore, because only one working electrode is required, the present invention can be utilized to determine corrosion rate in applications where the use of the two working electrode system is, if not impossible, at least impractical, such as rotating disc and rotating cylinder electrode systems, or any other high shear environment. Additionally, in the two working electrode system, it was unknown which electrode was corroding and thereby providing the data. In the present system, it is clearly established where the data originates, allowing good correlation between current and potential noise to be established. Finally, unlike the prior art, the size and geometry of the working electrode of the present invention is not limited.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. An electrochemical noise method for determining corrosion rate of an electrically conductive article, the method comprising:

placing a working electrode, a reference electrode, and a counter electrode in a corrosive environment of interest, wherein the working electrode has substantially the same composition as the electrically conductive article;

measuring potential at open circuit between the working electrode and the reference electrode over a first period of time;

placing the working electrode under a potentiostatic control;

measuring current between the working electrode and the counter electrode for a second period of time; and determining the corrosion rate of the electrically conductive article by dividing the measured current over time by the measured potential over time.

2. An electrochemical noise method for determining corrosion rate as in claim 1, wherein said first period of time and said second period of time are substantially equivalent.

3. An electrochemical noise method for determining corrosion rate as in claim 1, wherein, when under potentiostatic control, the working electrode is set at a potential substantially equivalent to the measured potential.

4. An electrochemical noise method for determining corrosion rate as in claim 3, wherein the set potential is substantially equivalent to the measured potential at the end of said first period of time.

5. The electrochemical noise measuring method for determining the corrosion rate as in claim 3, wherein the set potential is substantially equivalent to the open circuit potential at the end of the first period of time.

6. An electrochemical noise method for determining corrosion rate as in claim 1, wherein the counter electrode and the reference electrode are composed of a material which is substantially inert in the corrosive environment.

7. An electrochemical noise method for determining corrosion rate as in claim 1, further comprising repeating:

measuring potential at open circuit between the working electrode and the reference electrode over a first period of time;

placing the working electrode under a potentiostatic control; and measuring current between the working electrode and the counter electrode for a second period of time.

8. The electrochemical noise measuring method for determining the corrosion rate as in claim 1, wherein determining the corrosion rate of the article comprises determining the corrosion rate according to the proportionality $$I_{corr} \propto \frac{1}{R_N}$$

where $I_{corr}$ is the corrosion rate and $R_N$ is the ratio of the measured change in potential over time to the measured change in current over time.

9. The electrochemical noise measuring method for determining the corrosion rate as in claim 8 wherein $R_N$ is equal to the measured current over time divided by the measured potential over time.

10. The electrochemical noise measuring method for determining the corrosion rate as in claim 1, wherein placing the working electrode under potentiostatic control comprises placing the working electrode under potentiostatic control at the open circuit potential at the end of the first period.

11. The electrochemical noise measuring method for determining the corrosion rate as in claim 1, wherein said first period of time and said second period of time are independently preset.

12. An electrochemical noise corrosion measuring system, for determining the corrosion rate of an electrically conductive article, the system consisting of:

a working electrode having a composition substantially the same as the electrically conductive article;

a counter electrode which is substantially inert in an environment of interest;

a reference electrode which is substantially inert in the environment of interest;

a measurement system connected to the working electrode, the counter electrode, and the reference electrode, wherein the measurement system is capable of monitoring potential between the working electrode and the reference electrode and monitoring current between the counter electrode and the working electrode.

13. An electrochemical noise corrosion measuring system as in claim 12, wherein said measurement system is capable of automatically measuring potential at open circuit between the working electrode and the reference electrode over a first period of time; placing the working electrode under a potentiostatic control; and measuring current between the working electrode and the counter electrode for a second period of time.

14. An electrochemical noise corrosion measuring system, comprising:

a working electrode which is composed of a material of interest;

a counter electrode which is substantially inert in an environment of interest;

a reference electrode which is substantially inert in the environment of interest; and a measurement system connected to the working electrode, the counter electrode, and the reference electrode, for monitoring the potential between the working electrode and the reference electrode and monitoring the current between the counter electrode and the working electrode.

* * * * *

UNITED STATES PATENT AND TRADEMARK OFFICE
CERTIFICATE OF CORRECTION

PATENT NO. : 6,280,603 B1
DATED : August 28, 2001
INVENTOR(S) : Vladimir Jovancicevic

It is certified that error appears in the above-identified patent and that said Letters Patent is hereby corrected as shown below:

Column 1,
Line 42, before "corrosion" delete "me" and insert therefor -- the --

Column 4,
Line 11, delete formula "$I^L_{corr}{}^\sigma_i$," and insert therefor -- $I^L_{corr}{}^{\infty\sigma}_i$ --

Signed and Sealed this

Twenty-second Day of March, 2005

JON W. DUDAS
*Director of the United States Patent and Trademark Office*